United States Patent [19]

Smith et al.

[11] Patent Number: 5,171,874
[45] Date of Patent: Dec. 15, 1992

[54] PROCESS FOR MAKING DIHYDROCARBYL CARBONATE

[75] Inventors: David W. Smith; Steven D. Landau, both of Cincinnati, Ohio

[73] Assignee: Quantum Chemical Corporation, New York, N.Y.

[21] Appl. No.: 396,871

[22] Filed: Aug. 22, 1989

[51] Int. Cl.$^5$ .................. C07C 69/96; C07C 68/00
[52] U.S. Cl. .................. 558/260; 558/275; 558/277
[58] Field of Search .................. 558/260, 275, 277

[56] References Cited

U.S. PATENT DOCUMENTS

| | | | |
|---|---|---|---|
| Re. 29,338 | 8/1977 | Perrotti et al. | 558/277 |
| 3,952,045 | 4/1976 | Gaenzler et al. | 260/463 |
| 3,980,690 | 9/1976 | Cipriani et al. | 558/277 |
| 4,076,949 | 2/1978 | Zehner | 560/204 |
| 4,218,391 | 8/1980 | Romano et al. | 558/277 |
| 4,318,862 | 3/1982 | Romano et al. | 260/463 |
| 4,360,477 | 11/1982 | Hallgren et al. | 260/463 |
| 4,361,519 | 11/1982 | Hallgren | 260/463 |
| 4,426,331 | 1/1984 | Drent | 260/463 |
| 4,604,242 | 8/1986 | Harley et al. | 558/277 |
| 4,625,044 | 11/1986 | Curnutt | 558/277 |
| 4,636,576 | 1/1987 | Bhattacharya et al. | 558/277 |
| 4,638,076 | 1/1987 | Bhattacharya | 558/277 |

FOREIGN PATENT DOCUMENTS 8707601 12/1987 PCT Int'l Appl. .

*Primary Examiner*—Arthur C. Prescott
*Attorney, Agent, or Firm*—Kenneth D. Tremain; Gerald A. Baracka

[57] ABSTRACT

A process for making dihydrocarbyl carbonates is disclosed. In this process an alcohol having the structural formula R-OH, where R is alkyl, cycloalkyl or aralkyl, is reacted with oxygen and carbon monoxide in the presence of a heterogeneous copper-containing, halogen-free catalyst.

7 Claims, No Drawings

PROCESS FOR MAKING DIHYDROCARBYL CARBONATE

BACKGROUND OF THE DISCLOSURE

1. Field of the Invention

Dihydrocarbyl carbonates are important commercial compounds. The most important of these carbonates, dimethyl carbonate (DMC), for example, is used in enhancing the octane number of gasoline. Since octane enhancement of gasoline represents an immense market, and in view of the need to substitute non-lead containing compounds for this purpose, this compound has grown in commercial importance in recent years. The use of DMC has also been suggested for use as a less toxic and less polluting substitute for phosgene or dimethyl sulfate in reactions which normally require the use of one of these compounds.

A well known method of synthesizing dihydrocarbyl carbonates in general and DMC in particular involves the reaction of an alcohol, methanol in the case of synthesizing DMC, with carbon monoxide and oxygen in a catalytic oxidative carbonylation reaction. A plurality of references have been published directed to the major area of development in this process, the identity of the catalytic agent employed in the oxidative carbonylation reaction.

The processes of the prior art typically utilize a copper-containing catalyst. However, these copper-containing catalysts are characterized by the inclusion of halogen. Halogen is lost from the catalyst during the carbonylation reaction. Thus, replenishment of halogen is required during the reaction. To that end, at least one process of the prior art has suggested the introduction of a halogen source during the reaction. Usually, the halogen source is a hydrogen halide such as hydrogen chloride. These highly acidic agents introduce an important corrosion problem. Indeed, the use of a halogen-containing catalyst introduces corrosion problems necessitating the use of corrosion resistance process equipment, such as reactors, conduits and the like, in these carbonylation processes.

Another problem associated with the use of halogenated, usually chlorinated, catalysts is that in many cases the copper halide is not chemically bound to the catalytic support. As such, the reaction cannot occur in the liquid phase. The use of a liquid alkanol washes the catalytic agent from the catalyst support, increasing the rate of depletion. Thus, reactions utilizing catalysts with unbound copper halides on a support often occur in the gas phase. Those skilled in the art are aware that carbonylation reactions involving methanol are more efficiently run in the liquid phase.

To overcome these detrimental factors, some attempts have been made to utilize copper-containing catalysts which do not include halogen in the oxidative carbonylation of dihydrocarbyl carbonates. However, in these attempts, the catalyst utilized, although overcoming the detrimental feature of halogen containment, have been homogeneous. Those skilled in the art are aware that homogeneous catalysts are very difficult to separate from the product. This difficult separation, which results in not only loss of catalyst but, more importantly, product impurity, emphasizes the non-desirable nature of such homogeneous catalysts.

The above remarks establish the need in the art for a new catalytic process in the oxidative carbonylation of dihydrocarbyl carbonates synthesized from an alcohol, carbon monoxide and oxygen. Such a process should employ a catalyst which overcomes the problems associated with the catalytic agents used in the prior art.

2. Background of the Prior Art

A plurality of references describe processes in which carbon monoxide and oxygen are reacted with monohydric alcohols in general, alkanols in particular and methanol specifically, to produce esters in general, dialkyl carbonates in particular and dimethyl carbonate specifically. These references all involve the use of catalyst systems. These catalyst systems include at least one catalytic agent, oftentimes two or more. The more relevant of this body of prior art is discussed below.

U.S. Pat. No. 3,846,468 to Perrotti et al. is directed to a process in which an alcohol is reacted with oxygen and carbon monoxide in solution in the presence of a cuprous chloride complexed with an organic base bound to the copper atoms by coordinate bonds to produce dihydrocarbyl carbonates. This process is conducted in solution requiring the carbonate product separation from the catalyst by distillation.

U.S. Pat. No. 3,980,690 to Ciprani et al. describes a process related to the '468 patent. The primary distinction between the two processes is that the catalyst system is heterogeneous. The heterogeneous catalyst of the '690 patent consists of a complex of cuprous chloride and poly-4-vinyl pyridine.

Another process for forming carbonic acid esters is disclosed in U.S. Pat. No. 3,952,045 to Gaenzler et al. in which an alcohol is reacted with carbon monoxide and oxygen in the presence of a catalyst comprising copper chloride or copper bromide and an organic phosphorous compound. The copper chloride or copper bromide may be substituted with another copper salt. However, in that case a chloride or bromide of a metal other than copper, soluble in the reaction medium, is present in the reaction medium.

An oxidative carbonylation reaction involving the reaction of an alcohol with a mixture of carbon monoxide and oxygen is disclosed in U.S. Pat. No. 4,076,949 to Zehner. This process is characterized by the presence of a catalytic mixture of (1) a palladium, rhodium, platinum, copper or cadmium metal salt or mixture of such salts; (2) ammonia or an organic amine; (3) a copper or iron salt; and (4) an ammonium salt or an acid with a counterion other than a halide.

The catalytic agent in a reaction to form carbonic acid esters from the reactants, an alcohol, oxygen and carbon monoxide in U.S. Pat. No. 4,218,391 to Romano et al. is a cuprous or cupric salt having a single inorganic anion. Preferably, the copper salt is cuprous bromide, copper perchlorate or cuprous chloride.

The process of U.S. Pat. No. 4,318,862 to Romano et al. involves the formation of dimethyl carbonate by the reaction of methanol, oxygen and carbon monoxide in the presence of a copper salt catalyst. The improved feature of this process involves the utilization of an addition gaseous reactant, hydrogen, which produces hydrogen-enriched synthesis gas as a byproduct.

The carbonylation reaction of U.S. Pat. No. 4,360,477 to Hallgren et al. differs from the usual reaction of an alkanol with carbon monoxide and oxygen in that the reaction involves the recycling of an azeotropic mixture of methanol and dimethyl carbonate which then becomes the reactant. The catalyst used in this carbonylation reaction is cupric chloride or cupric bromide.

U.S. Pat. No. 4,361,519 to Hallgren describes another catalytic process for the preparation of dihydrocarbyl carbonates in which an alcohol is reacted with carbon monoxide and oxygen in the presence of a Group VIIIB noble metal, oxygen, a redox cocatalyst and a Bronsted base, which is an inorganic or organic base.

In an oxidative carbonylation reaction to produce carbonic acid esters from an alcohol, carbon monoxide and oxygen in the liquid phase, the process of U.S. Pat. No. 4,370,275 to Stamman et al. teaches the use of a catalyst system that includes copper and/or copper ions; one or more anions selected from the group consisting of an oxide anion, a hydroxide anion, a carbonate anion and mixtures thereof; halide ions; one or more nitrogen bases; and optionally, one or more ions of a Group II metal, a lanthanide group metal, an actinide group metal and/or a metal of atomic numbers 25 to 30.

The catalyst system of U.S. Pat. No. 4,426,331 to Drent to produce a carbonate ester from alcohol, carbon monoxide and oxygen includes a catalyst system which, in addition to a cuprous compound, comprises a sulfone.

A process for producing dihydrocarbyl carbonates which comprises contacting an alcohol in an oxidative carbonylation reaction with oxygen and carbon monoxide in which no halide is introduced is taught in U.S. Pat. No. 4,604,242 to Harley et al. In this process a homogeneous catalyst system, which comprises bis((2,4-pentanedianato)-copper(II)methoxide) and a basic nitrogen-containing coordination compound, is dissolved in the reaction solution. The carbonate product is thus obtained as part of an azeotrope with the alcoholic reactant.

The process of preparing a dihydrocarbyl carbonate from an alcohol, carbon monoxide and oxygen in U.S. Pat. No. 4,625,044 to Curnutt involves a vapor phase reaction with a catalyst which comprises a nitrogen-containing coordination compound-copper hydrocarbyloxy halide complex supported on activated carbon.

U.S. Pat. Nos. 4,636,576 and 4,638,076, both to Bhattacharya, disclose the preparation of dimethyl carbonate from methanol, carbon monoxide and oxygen in the presence of a catalyst system containing cupric methoxychloride. In the '576 patent the curpic compound of the catalyst system is supplemented with a nitrogen-containing cyclic amide. In the '076 patent the catalyst system includes a phosphoramide in addition to the aforementioned cupric compound.

A process for preparing dihydrocarbyl carbonates, comprising contacting an alkanol, carbon monoxide and oxygen, all in the vapor phase, with a heterogeneous catalyst which comprises a metal halide impregnated on a support, is set forth in PCT Publication WO 87/07601 to Curnutt. The metal of the metal halide is copper, nickel, iron or cobalt. Of these metals copper is preferred, with cupric chloride being the halide of choice. The above metal halide may also be supplemented with an alkali metal or alkaline earth metal chloride. The preferred support is activated carbon.

The above extensive analysis of the prior art establishes the absence therein of a non-halogen-containing heterogeneous copper catalyst. Thus, the problems mentioned above are not completely addressed by the extensive prior art related to processes for forming hydrocarbyl carbonates.

BRIEF SUMMARY OF THE INVENTION

A new process has now been discovered for making dihydrocarbyl carbonates. This process is conducted in the presence of a catalyst which although heterogeneous, and thus free of the problems associated with separating a homogeneous catalyst from the carbonate product, is halogen-free and therefore free of the difficulties of the prior art associated with the use of halogen-containing catalysts. The resultant process not only allows for longer term usage of a single catalytic charge compared to the halogen-containing catalysts of the prior art but, also, reduces the corrosion problem associated with the processes utilizing halogen-containing catalysts.

In accordance with the present invention a process is provided for making a dihydrocarbyl carbonate. In this process an alcohol, having the structural formula R—OH, where R is alkyl, cycloalkyl or aralkyl, is reacted with oxygen and carbon monoxide in the presence of a heterogeneous copper-containing, halogen-free catalyst.

DETAILED DESCRIPTION

The process of the present invention is directed to the synthesis of a dihydrocarbyl carbonate. This process involves an oxidative carbonylation reaction of an alcohol, oxygen and carbon monoxide. The alcohols within the contemplation of the present invention are characterized by the structural formula R—OH, where R is alkyl, cycloalkyl or aralkyl. Preferably, R is $C_1$–$C_6$ alkyl or benzyl. More preferably, R is $C_1$–$C_6$ alkyl. Still more preferably, R is $C_1$–$C_4$ alkyl. Most preferably, R is methyl, that is, the alcohol is methanol.

The oxidative carbonylation reaction of the present invention is catalyzed by a heterogeneous copper-containing, halogen-free catalyst. This heterogeneous copper-containing, halogen-free catalyst is either a catalyst formed by binding copper by ion exchange onto to a clay support or impregnating copper on a clay support.

The first class of catalysts within the scope of the present invention is a catalyst formed by binding copper by ion exchange onto a clay support. A preferred clay support in this ion exchange binding is a smectite, a class of naturally occurring clays. Of the smectite class of clays, the smectite subclasses of montmorillonite, hectorite and laponite, the synthetic analog of hectorite, are preferred. Of these subclasses, montmorillonite is most preferred.

In the process of binding copper by ion exchange onto a clay support, copper ions are ion exchanged onto the clay support by methods well known in the art. In a preferred embodiment a solution of a copper salt, other than a halide, such as copper nitrate or copper sulfate, is utilized to provide a source of copper ions. The preferred copper salt, in this application, is copper nitrate.

A second preferred class of heterogeneous catalysts within the contemplation of the present invention are catalysts formed by copper impregnation onto a clay support. In this catalyst system, the preferred copper source is elemental copper. It is preferred that the elemental copper be provided by impregnating copper ions onto the support followed by reduction of the copper ions to elemental copper.

A preferred clay support for copper impregnation is a metal pillared interlayered clay. Metal pillared interlayered clays are known in the art and are synthesized in accordance with known techniques. Preferred metals constituting the metal of the metal pillared interlayered clay useful in the formation of the catalyst include silicon, aluminum and zirconium. Silicon pillared interlayered clay is synthesized by methods disclosed in the U.S. Pat. No. 4,510,257, incorporated herein by reference. Aluminum pillared interlayered clay is synthesized in accordance with the procedures set forth in "Physical and Catalytic Properties of Hydroxy-Metal Interlayered Smectite Minerals" by Steven Landau, Ph.D. Disertation, Michigan State University, 1987. Zirconium pillared interlayered clay is synthesized in accordance with standard pillared clay forming techniques which are described in the above-referenced Landau dissertation. The Landau dissertation is incorporated herein by reference.

In the preferred embodiment wherein elemental copper is impregnated onto a metal pillared interlayered clay, a copper compound, preferably a copper (II) salt, is impregnated onto a metal pillared interlayered clay, preferably one of the aforementioned aluminum, silicon or zirconium pillared clays, and thereafter the impregnated copper ions are reduced to elemental copper. In a preferred embodiment this reduction is accomplished by hydrogenation. Surprisingly, the preferred salt utilized in the impregnation of the metal pillared interlayered clay is cupric chloride. It is emphasized, however, that the addition of hydrogen, to reduce the salt, also results in the removal of the chloride ions as gaseous hydrogen chloride.

The oxidative carbonylation reaction, encompassing the process of the present invention, preferably occurs either in a two phase liquid-gas reaction or totally in the gas phase. Preferably, the reaction occurs in a two phase liquid-gas reaction. That is, the methanol is reacted in the liquid phase with gaseous oxygen and carbon monoxide. The reactants are contacted with the catalyst of the present invention and are reacted at a pressure in the range of from atmospheric to about 1,000 psi. Preferably, the pressure of the reaction of the process of this invention is in the range of between about 50 psi and about 800 psi. More preferably, the pressure of this reaction is in the range of between about 200 psi and about 700 psi. Still more preferably, the pressure of the reaction is in the range of between about 550 psi and about 650 psi. The temperature at which the reaction occurs is preferably in the range of between about 25° C. and about 225° C. More preferably, the temperature of the reaction is in the range of between about 70° C. and about 180° C. Still more preferably, the temperature of the reaction is in the range of between about 70° C. and about 140° C.

The catalytic process of the present invention can occur in any reaction environment in which the catalyst contacts the reactants. Thus, the oxidative carbonylation reaction of the present process may occur with the catalyst disposed in a fixed bed, a fluidized bed or in a slurry. Of these methods, a fixed bed reaction demonstrates best results and is thus preferred.

The following examples are given to illustrate the scope of the present invention. Because these examples are given for illustrative purposes only, the invention should not be limited thereto.

EXAMPLE 1

Preparation of Copper Bound to Montmorillonite Catalyst

A naturally occurring smectite clay, montmorillonite, found in Arizona, acted as a support. Copper ions, having a +2 charge, were ion exchange bound to this Arizona montmorillonite by standard cationic exchange techniques. The copper ions, ion exchanged onto the Arizona montmorillonite, were provided by a solution of copper nitrate.

The final product, cupric ions ion exchange bound to Arizona montmorillonite, was analyzed. The product was found to include copper in a concentration of 11.8 weight percent, based on the total weight of the copper, supported on Arizona montmorillonite.

EXAMPLE 2

Formation of Purified Copper-Bound Montmorillonite

Arizona montmorillonite, of the type utilized in Example 1, was, unlike the catalyst of Example 1, purified. Purification of this montmorillonite clay was accomplished in accordance with the procedure set forth in *Data Handbook for Clay Materials and Other Non-Metallic Minerals*, H. Van Olphen and J. J. Fripiat, editors, Permagon Press, Elmsford, N.Y., 1979, incorporated herein by reference. The purification procedure resulted in the removal of non-lattice calcium and iron and the removal of organic contaminants. Copper was ion exchange bound to the thus purified Arizona montmorillonite in accordance with the procedure of Example 1, using copper nitrate to bind cupric ions to the support.

The copper bound by ion exchange to the purified Arizona montmorillonite support was analyzed and was found to contain 7.0 weight percent copper, based on the total weight of the copper-bound Arizona montmorillonite.

EXAMPLE 3

Oxidative Carbonylation of Methanol at 100° C. and 120° C.

A 15 inch long, ¾ inch Schedule 40 Hastelloy [trademark] C pipe was utilized as a reactor. Purified and unpurified Arizona montmorillonite to which cupric ions were bound by ion exchange, made in accordance with the procedures of Examples 1 and 2, respectively, were disposed in this pipe reactor to form a fixed bed reactor. Suitable conduit means in communication with oxygen, carbon monoxide and nitrogen gas cylinders and the inlet of the thus formed fixed bed reactor provided means for supplying these gases to the reactor. Similarly, methanol was supplied to the reactor by means of a methanol reservoir in communication, by suitable conduit means, to the inlet of the reactor. The rate of introduction of methanol was digitally controlled by a liquid chromatographic pump. The pressure in the reactor was provided by the gaseous reactants and controlled by a gas controller. The reactor was heated by a three-zone furnace, which was controlled by temperature controllers, and the resultant reactor temperature measured by a thermocouple.

The reactor was allowed to run at steady state with periodic liquid and gas sampling of the product stream which flowed into an outlet conduit. Two liquid samples per day were collected in a dry ice trap. Each sample was obtained over a two hour sampling period. Gas samples were withdrawn by a syringe from a sampling port disposed upstream of the dry ice trap and/or collected in gas bulbs downstream of the dry ice trap. Off gas volume was measured with a wet test meter.

The liquid samples were analyzed with a Chromosorb [trademark] 101 column on a Varian [trademark] 3700 gas chromatograph equipped with a flame ionization detector and a Spectra Physics [trademark] SP4000 integrator. Gas analysis was accomplished by using a thermal conductivity detector, employing a helium carrier on the analytical section of a CDS [trademark] 8100 automated reactor and a Hewlett-Packard [trademark] 3390A integrator.

In operation, the catalyst was disposed in the reactor in fixed bed configuration and pressurized with nitrogen gas to 600 psig. Carbon monoxide was thereafter introduced into the reactor at a rate of 250 standard cubic centimeters per minute to flush out the nitrogen. The reactor was then heated to the desired temperature. When the desired temperature was reached, methanol was pumped into the reactor at a rate of 0.3 ml/min. Oxygen was then introduced into the reactor at increasing flow rates until a final rate of 20 standard cubic centimeters per minute was reached.

The above described reaction, utilizing the described equipment, was run using as catalyst, copper ion exchange bound to purified and unpurified Arizona montmorillonite, that is, the catalyst of Examples 1 and 2, respectively. Runs were conducted at catalyst bed temperatures of 100° C. and 120° C. In each run the pressure in the reactor was maintained at 600 psig. The reactants, carbon monoxide, oxygen and methanol, were fed into the reactor at rates of 1,000 hr$^{-1}$, 160 hr$^{-1}$ and 1.2 hr$^{-1}$, respectively. It is emphasized that the carbon monoxide and oxygen were introduced as gases and the methanol as a liquid.

The results of these steady state experiments are summarized in Table I.

TABLE I

| | Dimethyl Carbonate Formation as a Function of Copper Ion Exchange Bound Catalyst | |
|---|---|---|
| | Mean Mole DMC/Mole Cu/Hr | |
| Bed Temp., °C. | Unpurified Cat. of Ex. 1 | Purified Cat. of Ex. 2 |
| 100 | .28 ± .02 | .22 ± .02 |
| 120 | .32 ± .06 | .29 ± .04 |

EXAMPLE 4

Oxidative Carbonylation of Methanol at 70° C. and 85° C.

Two additional runs, using the experimental equipment and procedure of Example 3, were conducted at two lower temperatures, 70° C. and 85° C. These runs were conducted using the copper on unpurified Arizona montmorillonite catalyst of Example 2. This test was conducted to determine the productivity and selectivity of the catalyst in synthesizing dimethyl carbonate The results of these runs are summarized in Table II. For completeness, the oxidative carbonylation results of the runs run at higher temperature using the same copper bound to unpurified Arizona montmorillonite catalyst, the catalyst of Example 3, are included in Table II.

TABLE II

| DMC Selectivity and Productivity as a Function of Fixed Bed Temperature Using the Catalyst of Example I | | | |
|---|---|---|---|
| | | DMC Selectivity, % | |
| Bed Temp, °C. | Productivity, moles DMC/l cat/hr | Based on CO | Based on Methanol |
| 70 | .14 ± .02 | 50 ± 7 | 37 ± 4 |

TABLE II-continued

| DMC Selectivity and Productivity as a Function of Fixed Bed Temperature Using the Catalyst of Example I | | | |
|---|---|---|---|
| | | DMC Selectivity, % | |
| Bed Temp, °C. | Productivity, moles DMC/l cat/hr | Based on CO | Based on Methanol |
| 85 | .37 ± .02 | 78 ± 3 | 88 ± 3 |
| 100 | .52 ± .06 | 69 ± 2 | 50 ± 4 |
| 120 | .64 ± .04 | 51 ± 4 | 28 ± 2 |

EXAMPLE 5

Oxidative Carbonylation of Methanol Using Other Clays

A series of screening experiments were conducted to determine the effectiveness of other smectite supported copper (II) ion exchange bound catalysts in the catalytic conversion of methanol to dimethyl carbonate.

The catalysts tested were formed by ion exchanging copper nitrate onto montmorrillonite obtained from Wyoming (Wyoming montmorillonite), hectorite, Laponite [trademark], a synthetic silicate and Barasym [trademark], another synthetic silicate. For comparison, a catalyst used in Examples 3 and 4, unpurified copper bound by ion exchange to Arizona montmorillonite, was also utilized in this test.

Each of the above catalysts (0.5 g.) were charged into a 71 ml glass-lined Parr [trademark] reactor with methanol (5 ml), air (200 psig) and carbon monoxide (400 psig). The reactor was heated to either 120° C. or 175° C. and shaken in an insulated box for 2 hours.

At the end of this time the reactor was cooled, the off gas was sampled and analyzed, in accordance with the procedure enumerated in Example 3, and the total gas volume determined. Liquid samples were analyzed by gas chromatography using a Chromosorb [trademark] 101 column. The results of these analyses are summarized in Table III.

TABLE III

| Oxidative Carbonylation of Methanol Using Cu Ion Exchanged Onto Clay Supports | | | | |
|---|---|---|---|---|
| Catalyst | | React. | Relative | |
| Smectite Support | Cu$^{+2}$ Conc., mmole | Temp, °C. | DMC Formed | CO$_2$ Formed, mmoles |
| Ariz. Montmor. | .93 | 175 | 11 | 4.4 |
| Ariz. Montmor. | .93 | 120 | 8 | 2.7 |
| Wyom. Montmor. | .28 | 175 | 7 | 2.6 |
| Hectorite | .44 | 175 | 3 | 0.9 |
| Laponite | .57 | 175 | 4 | 4.1 |
| Laponite | .57 | 120 | 1 | 0.4 |
| Barysym | .013 | 175 | 1 | 0.8 |

EXAMPLE 6 AND COMPARATIVE EXAMPLE 1

Oxidative Carbonylation of Methanol Utilizing Metal Pillared Interlayered Clay Support A series of four runs, two runs constituting Example 6 and two runs embodying Comparative Example 1, were conducted utilizing zirconium pillared interlayered clay. In the first of the two runs encompassing Comparative Example 1, zirconium pillared interlayered clay impregnated with cupric chloride was used as the catalyst. In the second of the two runs of Comparative Example 1, cupric chloride impregnated onto zirconium pillared interlayered clay was calcined prior to use.

The two runs conducted in accordance with Example 6 involved the impregnation of cupric chloride onto zirconium pillared interlayered clay followed by hydrogenation to reduce the copper (II) ions to elemental copper and, at the same time, to remove the chloride anions. The two runs of Example 6 differed by the inclusion of N₂O gas in one of the runs, as discussed below. The N₂O gas was utilized in order to suppress combustion.

The catalysts of Example 6 and Comparative Example 1 were used in an oxidative carbonylation of methanol reaction to produce dimethyl carbonate using the Parr [trademark] reactor described in Example 5. The quantity of reactants and catalysts were identical with that utilized in Example 5. That is, 0.5 g. of the catalysts; 5 ml methanol (123 mmoles); 400 psig carbon monoxide (61 mmoles); and 200 psig air (5.7 mmoles oxygen) were utilized. The additional gas, N₂O, also charged in the reaction in one of the runs of Example 6, was introduced into the Parr reactor at a pressure of 40 psig. The results of these runs, all conducted at 175° C., are included in Table IV.

TABLE IV

Oxidative Carbonylation of Methanol[(1)] Using Impregnated Zr. Pillared Interlayered Clay as Catalyst

| Exam. No. | Form of Impreg. Cu | Product, mmoles[(3)] | | |
|---|---|---|---|---|
| | | DMC | $CO_2$ | Dimethyl Ether |
| CE 1 | $CuCl_2$ | .03 | .67 | .78 |
| CE 1 | Calcined $CuCl_2$ | .49 | 3.4 | 2.5 |
| 6 | $H_2$ Reduced $CuCl_2$ | 1.6 | 3.0 | .53 |
| 6[(2)] | $H_2$ Reduced $CuCl_2$ | 1.4 | 2.3 | .26 |

[(1)]Run at 175° C., in which .5 g. catalyst, 5 ml. Methanol, 400 psi CO and 5.7 mmoles of $O_2$ (200 psi Air) were introduced into the reactor.
[(2)]Gas stream also contained $N_2O$ (40 psi).
[(3)]Theoretical yield is 11 mmoles of both DMC and $CO_2$ based on $O_2$.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for making dimethyl carbonate comprising reacting methanol with oxygen and carbon monoxide in the presence of a an elemental copper impregnated onto a metal pillared interlayered clay, halogen-free catalyst.

2. A process in accordance with claim 1 wherein said metal pillared interlayered clay is selected from the group consisting of zirconium pillared interlayered clay, aluminum pillared interlayered clay and silicon pillared interlayered clay.

3. A process for forming dimethyl carbonate comprising reacting methanol, oxygen and carbon monoxide in the presence of a copper impregnated onto a metal pillared interlayered clay, halogen-free catalyst at a pressure in the range of between atmospheric and about 1,000 psig and a temperature in the range of between about 25° C. and about 225° C.

4. A process in accordance with claim 3 wherein said process occurs at a pressure in the range of between about 50 psig and about 800 psig and at a temperature in the range of between about 70° C. and about 180° C.

5. A process in accordance with claim 4 wherein said catalyst is elemental copper impregnated onto zirconium pillared interlayered clay.

6. A process in accordance with claim 3 wherein said metal pillared interlayered clay is zirconium pillared interlayered clay.

7. A process in accordance with claim 6 wherein said process occurs at a pressure in the range of between about 200 psig and about 700 psig and a temperature in the range of between about 70° C. and about 140° C.

* * * * *